United States Patent [19]

Moore

[11] Patent Number: Plant 5,459

[45] Date of Patent: May 7, 1985

[54] MINIATURE ROSE PLANT

[75] Inventor: Ralph S. Moore, Visalia, Calif.

[73] Assignee: Sequoia Nursery, Visalia, Calif.

[21] Appl. No.: 530,732

[22] Filed: Sep. 9, 1983

[51] Int. Cl.[3] ..... A01H 5/00

[52] U.S. Cl. ..... Plt./8

[58] Field of Search ..... Plt./8

*Primary Examiner*—Robert E. Bagwill

[57] ABSTRACT

The subject of the present disclosure is a new and distinct variety of miniature rose plant characterized by (1) cream yellow buds and white flowers and (2) a plant completely free of thorns and prickles.

1 Drawing Figure

The present invention relates to a new and distinct variety of hardy, dwarf, bush type rose plant of the miniature class; the variety being primarily characterized—as to novelty—by cream to soft yellow buds and flowers which are cream to soft yellow and change to white. The general color effect being soft yellow to white.

The variety is further characterized by:

An abundance of bloom, with flowers, on mature plant, usually borne several to the stem in loose clusters.

Light fragrance.

A plant which is vigorous, of rounded somewhat spreading shape with semi-glossy to matt, small foliage with pointed leaflets; the main shoots and branches being completely free of thorns and prickles; the buds and flowers being similar in form to Yellow Doll (miniature—U.S. Plant Pat. No. 2,450, expired) but smaller in size.

The plant, which has a normal height of 14 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery, located at Visalia, Calif., under conditions of careful control and observation, as a cross between seedling #0-47-19 (Rosa Wichuriana × Floradora) as the seed parent and seedling #1-72-1 (Little Darling × Yellow Magic) a climbing miniature —not patented, as the pollen parent.

Subsequent to origination of the variety I successfully reproduced it, at Sequoia Nursery, located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to The British Colour Council Horticultural Colour Chart, except where common terms of color definition are employed.

Type: Hardy; dwarf; bushy; rounded — rather spreading; seedling; greenhouse; outdoors; cut flowers; garden decoration.

Class: miniature.

*International identifications.*—Variety MORfree. Commercial synonym: SOFTEE.

Flowers borne: Usually several together in clusters of 3–5 or more on slender wirey stems.

Quantity of bloom: Abundant both outside and in greenhouse.

Bud:

*Peduncle.*—Medium to long; slender but sturdy; erect; medium green, sometimes lightly tinted bronze (outdoors);

*Hairs.*—Few or none.

*Before calyx breaks.*—Size — small. Form long; pointed with several small foliaceous apendages and few or no hairs on surface of bud; with foliaceous parts extending beyond the tip of the bud equal to one-half or more of its length. Color — medium green, occasionally tinted with bronze (outdoors).

*As calyx breaks.*—Color — cream or pale yellow. Opening: opens well in all weather.

Bloom:

*Size when fully open.*—Small, averaging about 35–40 mm ($1\frac{1}{2}''$).

*Petalage.*—Double — averaging about 75 or more petals (15–20 being larger with the rest being very narrow and smaller) arranged regularly plus often several small petaloids.

*Form.*—High centered then becoming more rounded with petals reflexing loosely outward, and later at maturity, rolled loosely outward and downward. Open flowers may show stamens.

Petals: Fairly thick; satiny on inside and on outside surface.

*Shape.*—Outside petals, lanceolate with acute tip; intermediate — narrow lanceolate with acute tip; inside — narrow lanceolate with acute tip.

Color: (newly opened flower from a plant grown in plastic greenhouse (August 1983), Visalia, Calif.):

*Outside petal.*—Outside surface — near Mimosa Yellow 602/2 near base becoming white to near white at petal tip. Inside surface — similar to outside surface.

*Intermediate petal.*—Outside surface — near Mimosa Yellow 602/2 or Straw Yellow 604/2 at base becoming near Mimosa Yellow 602/2 on tip $\frac{1}{2}$. Inside surface — similar to outside surface.

*Inner petal.*—Outside surface — near Mimosa Yellow 602/2 or Straw Yellow 604/2. Inside surface — similar to outside surface. General color effect; newly opened flowers — white to near white on outer petals becoming cream to yellow on inner petals. Three days open — color changes to white or near white. Behavior — opens well in all weather. Color — pleasing blend of white to soft yellow. Spent petals drop off. Flower longevity (May 1983) — plant in pot 4–5 days or longer. Cut flowers at living room temperature 3–4 days.

Reproductive organs:

*Stamens.*—Few to several, arranged regularly about pistils.

*Filaments.*—Varying length, medium long, light yellow.

*Anthers.*—Yellowish.

*Pollen.*—Little to moderate amount.

*Pistils.*—Average number.

*Styles.*—Fairly even; medium to long length; bunched; color — yellowish.

*Ovaries.*—All enclosed in calyx.

*Hips.*—None to few.

*Sepals.*—Permanent; spear shape; recurved against peduncle.

*Seed.*—Few or none.

Foliage:

*Leaves.*—Compound of five (sometimes three or seven) leaflets; fairly small; leathery; semi-glossy to matt.

*Leaflets.*—Shape: broad, lanceolate; apex acute; base rounded. Margin serrate. Color: medium to dark green; new growth — normal (medium) green. Rachis: medium strength; upper side may have a few tiny short prickles or hairs, grooved; underside sparsely thorny (very small) with few or no tiny prickles. Stipules: medium long to long; narrow to medium width; short length; narrow points which turn out usually at about 45 degrees.

Growth:

*Habit.*—Dwarf; bushy; rounded to spreading; much branched.

*Growth.*—Free vigorous; internodes short.

*Canes.*—Medium slender; sturdy.

*Main stems.*—Color: medium green.

*Thorns.*—None. Prickles — none.

*Branches.*—Color: medium green. Thorns: none. Prickles: none. Hairs: none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, rounded, to spreading, much branched habit, substantially as illustrated and described, characterized by buds and flowers of a cream to soft yellow color which changes to white, the bud and flower resembling the variety Yellow Doll (U.S. Plant Pat. No. 2,450, expired) in form but smaller in size; and further characterized by a plant of vigorous and compact growth habit, with main canes and branches completely thornless, easy to propagate from cuttings or by budding, with an abundance of small to medium size semi-glossy to matt foliage and an abundance of flowers borne usually in loose clusters of 3 to 5 or more.

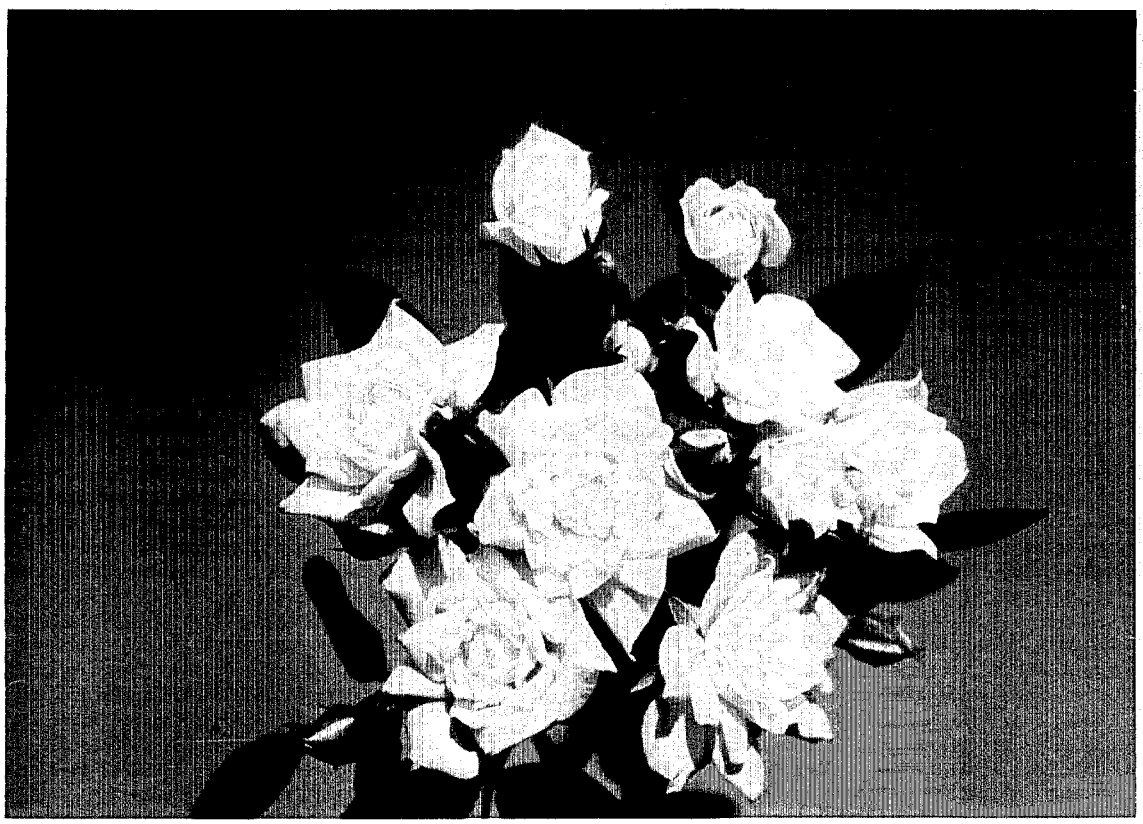

* * * * *